(12) United States Patent
Andreella et al.

(10) Patent No.: US 8,063,041 B2
(45) Date of Patent: Nov. 22, 2011

(54) POLYMORPHIC FORM D OF BAZEDOXIFENE ACETATE AND METHODS OF PREPARING SAME

(75) Inventors: Paolo Andreella, Legnago (IT); Roberto Brescello, Abano Terme (IT); Ivan Michieletto, Venezia (IT); Mauro Maffini, Zevio (IT); Nicola Catozzi, Isola Vicentina (IT); Andrea Nicoli, Vicenza (IT); Paolo Fornasari, Bondeno (IT); Massimo Verzini, Caldiero (IT); Livius Cotarca, Cervignano del Friuli (IT); Franco Brazzarola, San Bonifacio (IT)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/820,593

(22) Filed: Jun. 22, 2010

(65) Prior Publication Data

US 2011/0021504 A1  Jan. 27, 2011

Related U.S. Application Data

(60) Provisional application No. 61/244,961, filed on Sep. 23, 2009.

(30) Foreign Application Priority Data

Jun. 23, 2009  (IT) .............................. MI2009A1109

(51) Int. Cl.
*A61P 19/00*  (2006.01)
*A61K 31/55*  (2006.01)
*C07D 403/00*  (2006.01)
(52) U.S. Cl. ................... 514/217.08; 540/602
(58) Field of Classification Search ............. 514/217.08; 540/602
See application file for complete search history.

(56) References Cited

U.S. PATENT DOCUMENTS

| 5,998,402 | A | 12/1999 | Miller et al. | |
| 2005/0227965 | A1* | 10/2005 | Demerson et al. | 514/217.08 |
| 2005/0227966 | A1* | 10/2005 | Shah et al. | 514/217.09 |

FOREIGN PATENT DOCUMENTS

| WO | WO-2005100314 A1 | 10/2005 |
| WO | WO-2005100316 A1 | 10/2005 |

OTHER PUBLICATIONS

International Search Report and Written Opinion from International Application No. PCT/US2010/039488 mailed Sep. 15, 2010. 11 pages.

* cited by examiner

*Primary Examiner* — Brenda Coleman
(74) *Attorney, Agent, or Firm* — Ram W. Sabnis; A. David Joran

(57) ABSTRACT

The present disclosure relates to polymorphic Form D of bazedoxifene acetate, pharmaceutical compositions and methods of treatment using the same, and methods of preparing the same.

5 Claims, 7 Drawing Sheets

POLYMORPHIC FORM D OF BAZEDOXIFENE ACETATE AND METHODS OF PREPARING SAME

CROSS-REFERENCE

This application is a non-provisional application which claims the benefit of U.S. Provisional application 61/244,961, filed Sep. 23, 2009, and Italian Patent application MI2009A001109, filed Jun. 23, 2009.

TECHNICAL FIELD

The present disclosure relates to a novel polymorphic form of bazedoxifene acetate, methods of preparing the polymorphic form, and compositions and methods of treatment using the polymorphic form.

BACKGROUND

Bazedoxifene acetate has a chemical name of (1-[4-(2-azepan-1-yl-ethoxy)-benzyl]-2-(4-hydroxy-phenyl)-3-methyl-1H-indol-5-ol acetic acid) and has the chemical structure shown below:

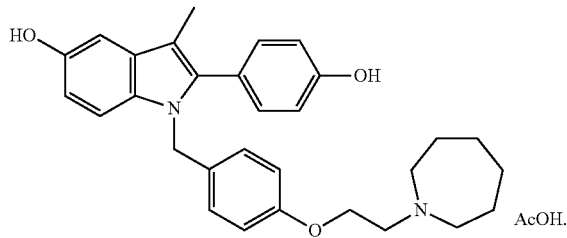

Bazedoxifene acetate belongs to the class of drugs typically referred to as selective estrogen receptor modulators (SERMs). Consistent with its classification, bazedoxifene demonstrates affinity for estrogen receptors (ER) but shows tissue selective estrogenic effects. For example, bazedoxifene acetate demonstrates little or no stimulation of uterine response in preclinical models of uterine stimulation. Conversely, bazedoxifene acetate demonstrates an estrogen agonist-like effect in preventing bone loss and reducing cholesterol in an ovariectomized rat model of osteopenia. In an MCF-7 cell line (human breast cancer cell line), bazedoxifene acetate behaves as an estrogen antagonist. These data demonstrate that bazedoxifene acetate is estrogenic on bone and cardiovascular lipid parameters and antiestrogenic on uterine and mammary tissue and thus has the potential for treating a number of different disease or disease-like states in which the estrogen receptor is involved. See, for example, U.S. Pat. Nos. 5,998,402 and 6,479,535 and Miller, et al., *Drugs of the Future*, 2002, 27(2), 117-121, for further description of the bazedoxifene acetate's biological activity.

It is well known that the crystalline polymorph form of a particular drug is often an important determinant of the drug's ease of preparation, stability, solubility, storage stability, ease of formulation and in vivo pharmacology. Polymorphic forms occur where the same composition of matter crystallizes in a different lattice arrangement resulting in different thermodynamic properties and stabilities specific to the particular polymorph form. Different polymorphs of a given compound may differ from each other with respect to one or more physical properties, such as solubility and dissociation, true density, crystal shape, compaction behavior, flow properties, and/or solid state stability. In cases where two or more polymorph substances can be produced, it is desirable to have a method to make each polymorph in pure form. In deciding which polymorph is preferable in a given situation, the numerous properties of the polymorphs must be compared and the preferred polymorph chosen based on the many physical property variables. It is entirely possible that one polymorph form can be preferable in some circumstances where certain aspects such as ease of preparation, stability, etc. are emphasized. In other situations, a different polymorph may be preferred, e.g., for greater solubility and/or superior pharmacokinetics. However, preparing a polymorphic form of a drug involves many challenges because not only is it difficult to predict which polymorphic form will crystallize under certain conditions, it is also difficult to find conditions which will prevent conversion of one polymorph form to another.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In addition, the materials, methods, and examples are illustrative only and not intended to be limiting.

SUMMARY

Disclosed herein is a polymorph of bazedoxifene acetate, wherein the polymorph is a substantially pure polymorph of Form D. Compositions including Form D in combination with one or more other polymorphic crystalline or amorphous forms, e.g., bazedoxifene acetate Forms A-C are also contemplated. Also provided are methods for the preparation of bazedoxifene acetate polymorph Form D, pharmaceutical compositions including Form D, and methods of treatment using the same.

In an aspect, the present disclosure provides a crystalline polymorph of Form D having an X-ray powder diffraction (XRPD) pattern comprising characteristic peaks, in terms of 2θ, at about 10.6°, 14.0°, 17.1°, 17.5° and 24.2°. In at least some embodiments, the polymorph has an XRPD pattern substantially as shown in FIG. 1. In some embodiments, the polymorph has a Raman spectrum substantially as shown in FIG. 2. In at least some embodiments, the polymorph has a differential scanning calorimetry (DSC) trace substantially as shown in FIG. 3. In at least embodiments, the polymorph has a temperature of glass transition between about 166° C. and 168° C.

The disclosure further provides compositions comprising bazedoxifene acetate polymorph Form D and a pharmaceutically acceptable carrier. In some embodiments, the pharmaceutically acceptable carrier is suitable for oral administration and the composition comprises an oral dosage form. In some embodiments, at least about 50-99% by weight of the total of bazedoxifene acetate in the composition is present as the polymorph Form D. In further embodiments, at least about 70%, at least about 80%, or at least about 90% by weight of the total of bazedoxifene acetate in the composition is present as the polymorph. Also provided by the disclosure are compositions consisting essentially of bazedoxifene acetate wherein at least about 97-99% by weight of the bazedoxifene acetate is present in the composition as the polymorph Form D.

In other aspects, the disclosure provides methods of treating a disease or disorder associated with estrogen deficiency or estrogen excess, in an animal in need thereof, which comprises, administering an effective dose of a composition containing bazedoxifene acetate Form D. In some embodiments, the disease or disorder associated with estrogen deficiency or estrogen excess is selected from the group consisting of osteoporosis, prostatic hypertrophy, male pattern baldness, vaginal and skin atrophy, acne, dysfunctional uterine bleeding, endometrial polyps, benign breast disease, uterine leiomyomas, adenomyosis, ovarian cancer, infertility, breast cancer, endometriosis, endometrial cancer, polycystic ovary syndrome, cardiovascular disease, contraception, Alzheimer's disease, cognitive decline, melanoma, prostate cancer, cancers of the colon, and CNS cancers.

In another aspect, the disclosure provides methods of treating a disease or disorder associated with proliferation or abnormal development of endometrial tissues, in an animal in need thereof, which comprises, administering an effective dose of a composition containing bazedoxifene acetate Form D. In some embodiments, the disease or disorder associated with proliferation or abnormal development of endometrial tissues is selected from the group consisting of endometrial polyps, endometriosis, and endometrial cancer.

In another aspect, the disclosure provides methods of lowering cholesterol, inhibiting bone loss, or treating breast cancer, in an animal in need thereof, which comprises administering an effective dose of a composition containing bazedoxifene acetate Form D. In some embodiments, the bone loss results from a disease or disorder selected from the group consisting of osteoporosis, osteopenia, osteoarthritis, hypocalcemia, hypercalcemia, Paget's disease, osteomalacia, osteohalisteresis, multiple myeloma and cancer.

In yet another aspect, the disclosure provides methods of treating perimenopausal, menopausal, or postmenopausal symptoms, in an animal in need thereof, which comprises administering an effective dose of a composition containing bazedoxifene acetate Form D. In some embodiments, the perimenopausal, menopausal, or postmenopausal symptom is a vasomotor disturbance, such as a hot flush.

The disclosure also provides a method of preparing polymorphic Form D of bazedoxifene acetate, the method comprising: (a) contacting hexamethylenimino benzyloxyindole with hydrogen in a solvent comprising ethanol, and in the presence of a catalyst at elevated temperature to provide a first reaction mixture comprising bazedoxifene free base, wherein the first reaction mixture is substantially free from hexamethylenimino benzyloxyindole; (b) treating said first reaction mixture with an antioxidant to provide a second reaction mixture; (c) filtering said second reaction mixture to provide a solution comprising bazedoxifene free base; and (d) treating said solution with acetic acid to crystallize polymorphic Form D of bazedoxifene acetate.

In a further aspect, the present disclosure relates to a polymorphic Form D of bazedoxifene acetate prepared according to the methods described herein.

Other features and advantages of the disclosure will be apparent from the detailed description, drawings, and from the claims.

BRIEF DESCRIPTIONS OF THE DRAWINGS

DETAILED DESCRIPTION

The present disclosure provides a novel polymorph Form D of the compound 1-[4-(2-azepan-1-yl-ethoxy)-benzyl]-2-(4-hydroxy-phenyl)-3-methyl-1H-indol-5-ol acetic acid (bazedoxifene acetate), having the following formula:

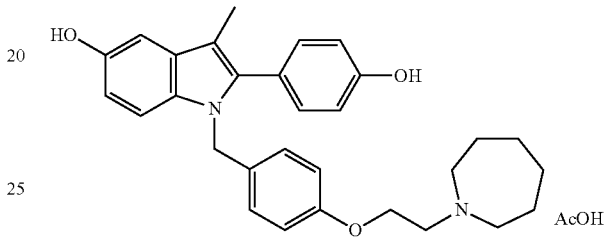

In addition to polymorph Form D of the disclosure, other known polymorphs of bazedoxifene acetate include crystalline polymorph Forms A and B and amorphous Form C.

As used herein, a "polymorph" refers to different crystalline forms of the same compound and includes, but is not limited to, other solid state molecular forms including hydrates and solvates of the same compound. Different polymorphs of a given compound may differ from each other with respect to one or more physical properties, such as solubility and dissociation, true density, crystal shape, compaction behavior, flow properties, and/or solid state stability. Unstable polymorphs generally convert to the more thermodynamically stable forms at a given temperature after a sufficient period of time. Metastable forms are unstable polymorphs that slowly convert to stable forms. In general, the stable form exhibits the highest melting point and the most chemical stability; however, metastable forms may also have sufficient chemical and physical stability to render them pharmaceutically acceptable. "Chemical stability" as used herein refers to the stability of certain chemical properties, including but not limited to thermal stability, light stability, and moisture stability.

The polymorph form D of bazedoxifene acetate is in some embodiments substantially pure, meaning the polymorph form includes less than about 15%, less than about 10%, less than about 5%, or less than about 1% by weight of impurities, including other polymorph forms of bazedoxifene acetate.

The polymorph form D can also be present in mixtures. In some embodiments, polymorph Form D can be present in mixtures with other polymorph Forms A and/or B, and/or amorphous bazedoxifene acetate (Form C). Compositions containing multiple polymorphic forms can be prepared by any suitable method, including admixture of Form D prepared as described herein with substantially pure Forms A and/or B made, for example, according to any of the processes described previously in International Publications WO 2005/100316, WO 2005/100314, and U.S. Provisional Patent Application No. 61/027,725, the disclosures of each of which are herein incorporated by reference in their entireties.

Respective amounts of polymorphic forms of bazedoxifene acetate in a composition can be determined by any suitable spectroscopic method, such as X-ray powder diffraction or differential scanning calorimetry.

Figure 1:
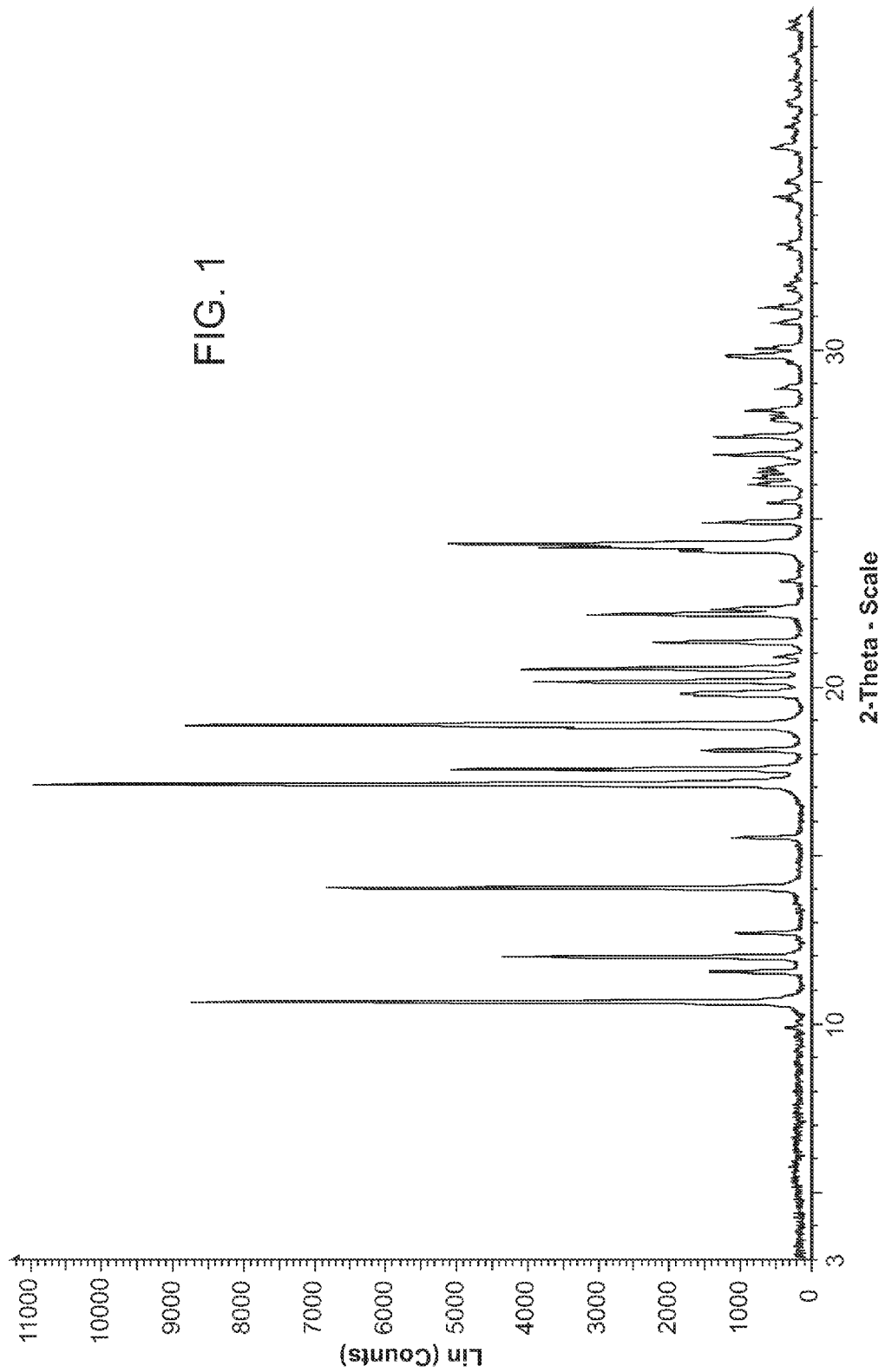
FIG. 1 shows a characteristic X-Ray Powder Diffraction (XRPD) pattern of polymorph Form D of bazedoxifene acetate.

Polymorph Form D can be identified by one or more solid state analytical methods. For example, Form D can be identified by a powder X-ray diffraction pattern substantially as shown in FIG. 1. Powder X-ray diffraction data consistent with Form D is provided in Table 1 below. As is understood by those skilled in the art, the relative intensities of the peaks can vary, depending upon the sample preparation technique, the sample mounting procedure and the particular instrument employed. Moreover, instrument variation and other factors can affect the 2-theta values to some extent.

TABLE 1

| Angle 2-Theta ° (±0.1) | Intensity % | Angle 2-Theta ° (±0.1) | Intensity % |
|---|---|---|---|
| 9.838 | 3.2 | 27.427 | 12.5 |
| 10.612 | 79.7 | 27.937 | 4.6 |
| 11.513 | 12.8 | 28.084 | 5.2 |
| 11.950 | 39.7 | 28.210 | 8.4 |
| 12.668 | 9.6 | 28.881 | 4.6 |
| 14.018 | 62.2 | 28.963 | 2.9 |
| 15.506 | 10.2 | 29.614 | 3.0 |
| 17.091 | 100.0 | 29.827 | 10.6 |
| 17.541 | 46.2 | 30.054 | 6.9 |
| 18.110 | 14.0 | 30.821 | 5.0 |
| 18.859 | 80.5 | 30.904 | 3.4 |
| 19.797 | 16.7 | 31.281 | 6.7 |
| 20.147 | 35.6 | 31.785 | 2.8 |
| 20.519 | 37.1 | 31.944 | 3.3 |
| 20.897 | 4.6 | 32.027 | 2.5 |
| 21.321 | 20.1 | 33.024 | 2.7 |
| 22.150 | 28.8 | 33.156 | 4.2 |
| 22.310 | 12.9 | 33.255 | 2.6 |
| 23.135 | 3.8 | 34.462 | 3.2 |
| 24.023 | 16.9 | 34.561 | 4.5 |
| 24.143 | 35.0 | 35.029 | 2.7 |
| 24.235 | 46.4 | 36.027 | 5.0 |
| 24.879 | 13.9 | 36.655 | 3.2 |
| 25.478 | 5.6 | 37.294 | 2.9 |
| 26.020 | 7.8 | 37.410 | 3.3 |
| 26.215 | 7.3 | 38.030 | 2.8 |
| 26.387 | 6.7 | 38.755 | 2.7 |
| 26.503 | 6.6 | 39.579 | 3.1 |
| 26.903 | 12.4 | 39.795 | 2.6 |

Figure 2:
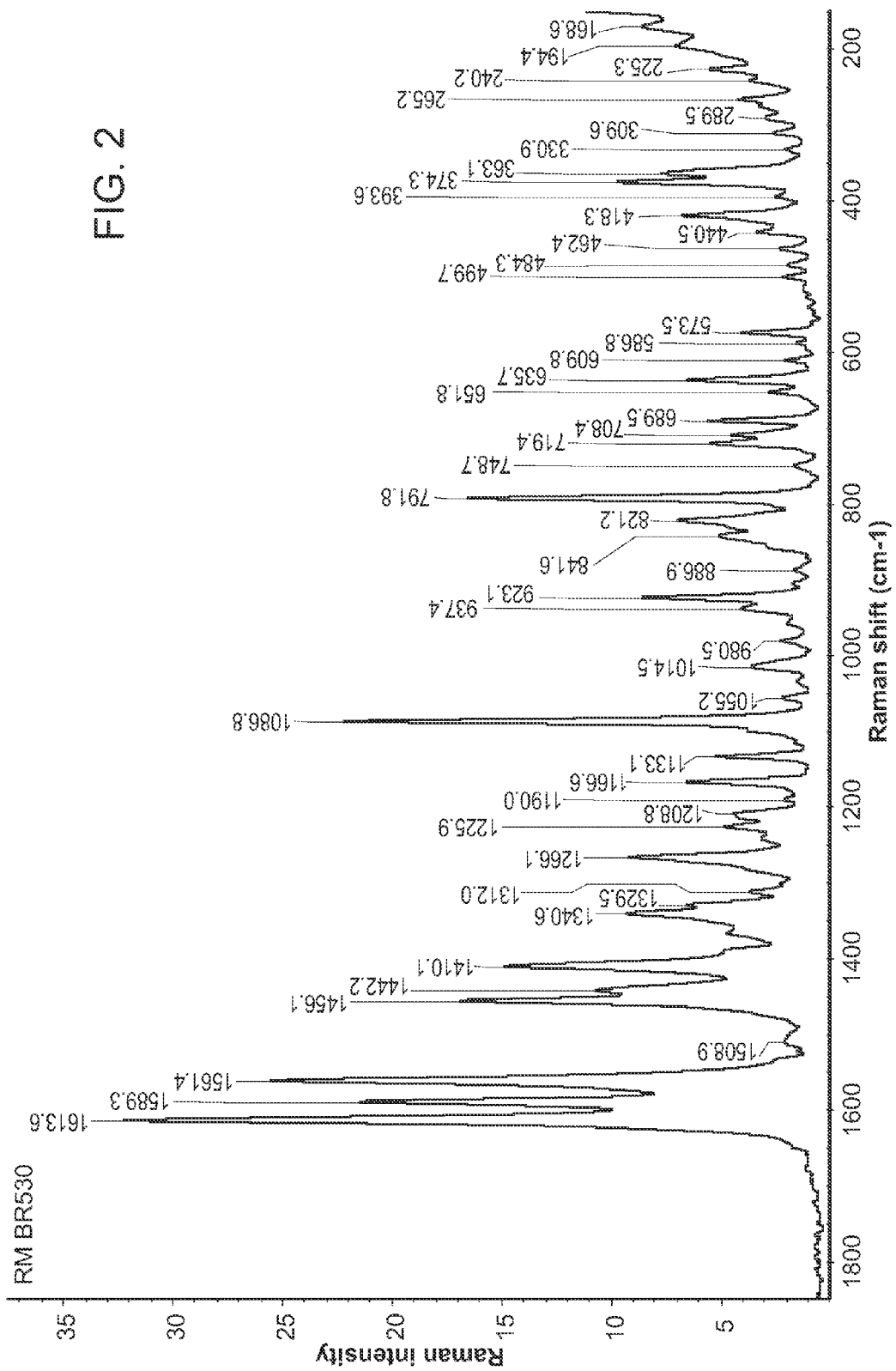
FIG. 2 shows a characteristic Raman spectrum of polymorph Form D of bazedoxifene acetate.
Figure 2:
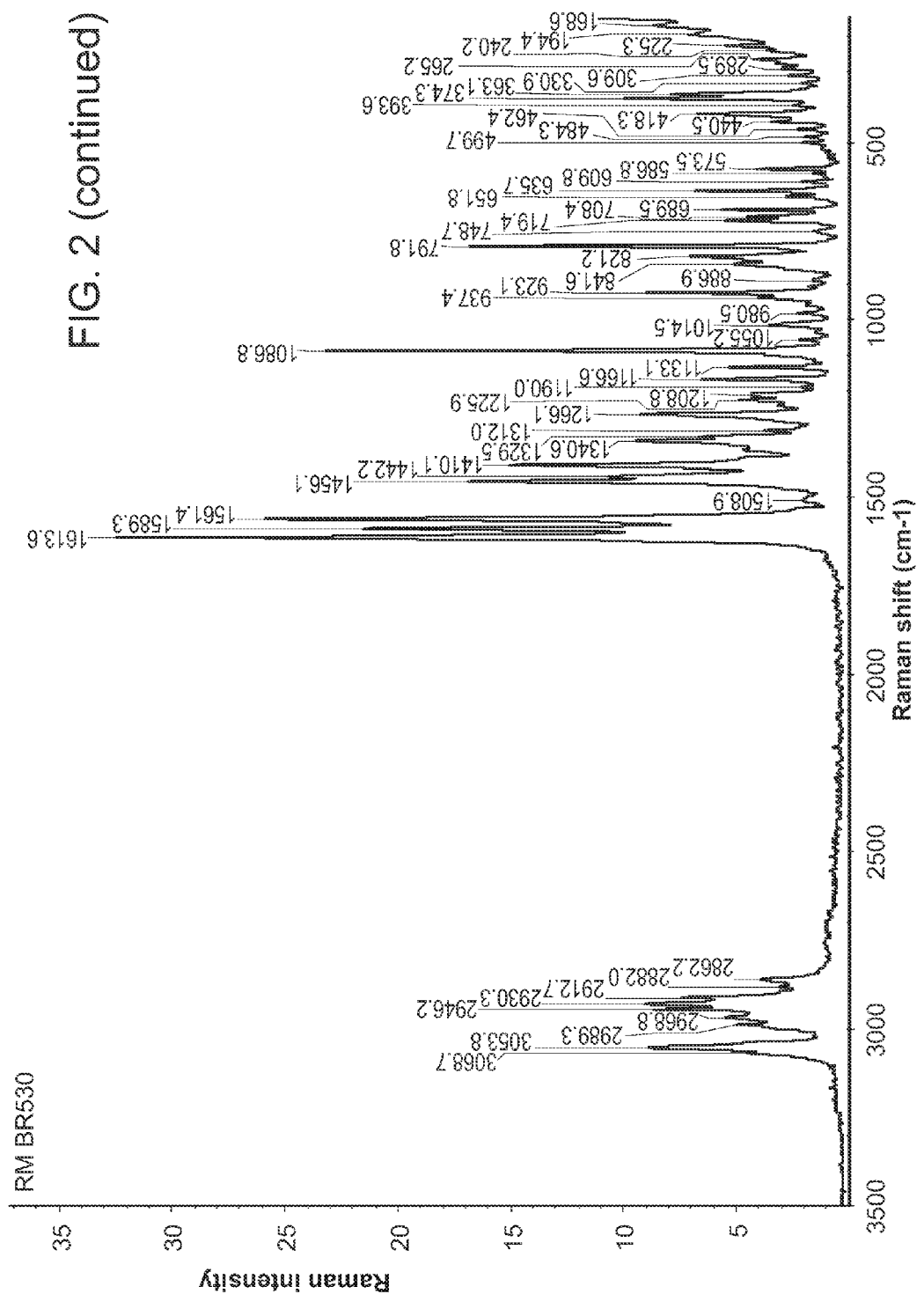

Polymorph Form D can also be identified by its characteristic Raman spectrum substantially as shown in FIG. 2. In some embodiments, Form D is characterized by a Raman spectrum having one or more characteristic peaks selected from about 1561 $cm^{-1}$, about 1589 $cm^{-1}$ and about 1613 $cm^{-1}$.

Figure 3:
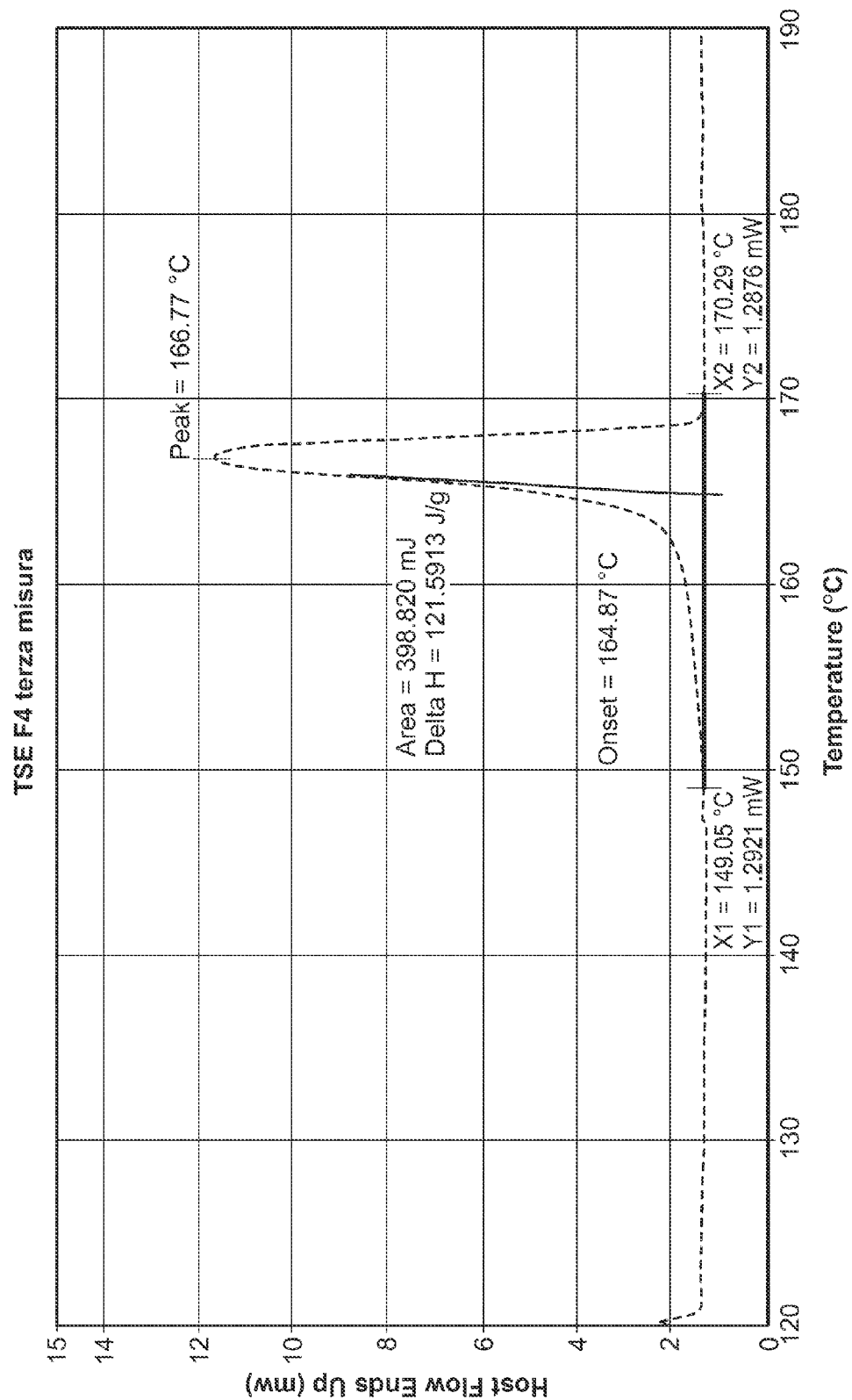
FIG. 3 shows a characteristic DSC thermogram of polymorph Form D of bazedoxifene acetate.

Polymorph Form D can also be identified by its characteristic DSC trace substantially as shown in FIG. 3. In at least some embodiments, Form D is characterized by a temperature of glass transition between about 166° C. and about 168° C. One skilled in the art will appreciate that depending on the rate of heating, i.e. scan rate, at which the DSC analysis is conducted, the calibration standard used, instrument calibration, the relative humidity and the relative purity, the endotherms of the polymorphs may vary by about 0.01-10° C., or about 0-5° C., above or below the determined endotherms. The observed endotherm may also differ to some extent from instrument to instrument for any given sample.

For purposes of administration, polymorph Form D of bazedoxifene acetate may be formulated in substantially pure form, or mixed with other polymorphic crystalline or amorphous forms of bazedoxifene acetate, as a pharmaceutical composition. Pharmaceutical compositions in certain embodiments comprise one or more polymorphs of bazedoxifene acetate and a pharmaceutically acceptable carrier, wherein the bazedoxifene acetate is present in the composition in an amount that is effective to treat the condition, disease or disorder of interest. As used herein, "treatment" of a condition includes partial or complete prevention and/or amelioration of symptoms and/or disease state. The concentration of the compounds described herein in a therapeutic composition will vary depending upon a number of factors, including the dosage of the drug to be administered and the route of administration. Appropriate concentrations and dosages can be readily determined by one skilled in the art.

In at least some embodiments, bazedoxifene acetate may be administered according to an extended dosing regimen ranging from once every two days, to once per week. The dosage for a given dosing regimen can be given all at once or given multiple times on the same day. Based on individual patient needs, bazedoxifene acetate may be administered every second day, every third day, every fourth day, every fifth day, every sixth day, or every seventh day (once weekly). The administration period may also be adjusted depending on the needs of the patient, and still be considered to be administered according to an extended dosing regimen.

For example, the dosage may be given once every other day, and then after medical follow-up be adjusted to be administered every third day, and eventually once weekly. The extended dosing regimen may be administered once weekly, where the weekly dosage is given on one day, either as a single dose, or divided into two or more doses during the same day.

In at least some embodiments, the daily dosage of bazedoxifene acetate in humans is between about 5-80 mg. When bazedoxifene acetate is administered once weekly, the once per week dosage in at least some embodiments will be from about 3-15 times that of the daily dosage. Accordingly, in at least some embodiments the once weekly oral dosage may be between about 15 and 1200 mg given once per week; with the dosage being given in one or more doses during the administration day.

In some embodiments, at least about 50-99% by weight of the total of bazedoxifene acetate in the composition is present as the polymorphic Form D bazedoxifene acetate prepared as described herein. In further embodiments, at least about 70%, at least about 80%, at least about 90%, at least about 95%, at least about 97%, at least about 98%, at least about 99%, at least about 99.5%, or at least about 99.9% by weight of the total of bazedoxifene acetate in the composition is present as polymorph Form D. Also provided by the disclosure are compositions consisting essentially of bazedoxifene acetate wherein at least about 97-99% by weight of the bazedoxifene acetate is present in the composition as polymorph Form D.

The methods of the present disclosure include systemic administration of a polymorph as disclosed herein, for example in the form of a pharmaceutical composition. These methods include the step of administering, to an animal in need thereof, an effective dose of a pharmaceutical composition comprising a polymorph of bazedoxifene acetate and a pharmaceutically acceptable carrier. One skilled in the art may formulate the compositions in an appropriate manner, and in accordance with accepted practices, such as those described in *Remington's Pharmaceutical Sciences* (Gennaro, Ed., Mack Publishing Co., Pa. 1990). Examples of suitable formulations of bazedoxefine acetate include those described in International Publications WO 0203987, WO 03105834, and WO 07024961, the disclosures of each of which are herein incorporated by reference in their entireties.

Oral formulations containing the active compounds of this disclosure may comprise any conventionally used oral forms, including tablets, capsules, buccal forms, troches, and lozenges. Capsules may contain mixtures of the active compound(s) with inert fillers and/or diluents such as pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, 30 carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

As described in U.S. Pat. No. 5,998,402, bazedoxifene and salts thereof are selective estrogen agonists with affinity for the estrogen receptor. Unlike other types of estrogen agonists, bazedoxifene and salts thereof are antiestrogenic in the uterus and can antagonize the trophic effects of estrogen agonists in uterine tissues. Accordingly, polymorphs of bazedoxifene acetate and compositions containing the same can find many uses related to treating disease states or syndromes associated with estrogen deficiency or excess of estrogen. In some embodiments, the disclosure provides methods of treating a disease or disorder associated with estrogen deficiency or estrogen excess. Diseases and disorders associated with estrogen deficiency or estrogen excess include bone loss, osteoporosis, prostatic hypertrophy, male pattern baldness, vaginal and skin atrophy, acne, dysfunctional uterine bleeding, endometrial polyps, benign breast disease, uterine leiomyomas, adenomyosis, ovarian cancer, infertility, breast cancer, endometriosis, endometrial cancer, polycystic ovary syndrome, cardiovascular disease, contraception, Alzheimer's disease, cognitive decline and other CNS disorders, as well as certain cancers including melanoma, prostate cancer, cancers of the colon, and CNS cancers, among others.

Polymorphs of bazedoxifene acetate can also be used in methods of treatment for diseases or disorders which result from proliferation or abnormal development, actions or growth of endometrial or endometrial-like tissues. In some embodiments, the disclosure provides methods of treating a disease or disorder associated with proliferation or abnormal development of endometrial tissues. Diseases and disorders associated with proliferation or abnormal development of endometrial tissues include endometrial polyps, endometriosis, and endometrial cancer.

The polymorph of the disclosure can also be used in methods of inhibiting bone loss. Bone loss often results from an imbalance in an individual's formation of new bone tissues and the resorption of older tissues, leading to a net loss of bone. Such bone depletion can occur in a range of individuals, for example in post-menopausal women (e.g., women experiencing post-menopausal osteoporosis or osteopenia), women who have undergone bilateral oophorectomy, those receiving or who have received extended corticosteroid therapies, those experiencing gonadal dysgenesis, and those suffering from Cushing's syndrome. Special needs for bone, including teeth and oral bone replacement, can also be addressed using the polymorph in individuals with bone fractures, defective bone structures, and those receiving bone-related surgeries and/or the implantation of prosthesis. In addition to the problems described above, in some embodiments the polymorph can be used in treatments for osteoporosis, osteopenia, osteoarthritis, hypocalcemia, hypercalcemia, Paget's disease, osteomalacia, osteohalisteresis, multiple myeloma and other forms of cancer having deleterious effects on bone tissues.

The polymorphic form of bazedoxifene acetate can also be used in methods of lowering cholesterol and treating breast cancer. Additionally, the polymorph can be used for treating perimenopausal, menopausal, or postmenopausal symptoms. In some embodiments, the polymorphs can be used for contraception in pre-menopausal women, as well as hormone replacement therapy in post-menopausal women (such as for treating vasomotor disturbances such as hot flush) or in other estrogen deficiency states where estrogen supplementation would be beneficial. The polymorphs can also be used in disease states where amenorrhea is advantageous, such as leukemia, endometrial ablations, chronic renal or hepatic disease, or coagulation diseases or disorders.

In one aspect, the present disclosure provides a method of preparing polymorphic Form D of bazedoxifene acetate, the method comprising: (a) dissolving polymorphic Form A of bazedoxifene acetate in a solvent comprising ethyl acetate at elevated temperature to form a solution; and (b) cooling the solution to crystallize polymorphic Form D of bazedoxifene acetate.

In certain embodiments, in step (a) of the method described herein, said elevated temperature is at about 30° C. or higher. In certain other embodiments, the elevated temperature is at about 40° C. or higher. In certain other embodiments, the elevated temperature is at about 50° C. or higher. In certain other embodiments, the elevated temperature is at about 60° C. or higher.

In certain other embodiments, step (a) of the method described herein is conducted in the presence of an antioxidant. In some embodiments, the antioxidant is ascorbic acid.

In certain embodiments, in step (b) of the method described herein, the solution is cooled to about 40° C. or lower. In some embodiments, the solution is cooled to about 30° C. or lower. In certain other embodiments, the solution is cooled to between about 0° C. to about 30° C.

In certain embodiments, in step (b) of the method described herein, crystallization is facilitated by seeding with polymorphic Form D of bazedoxifene acetate.

In one aspect, the present disclosure provides a method of preparing polymorphic Form D of bazedoxifene acetate, the method comprising: (a) contacting hexamethylenimino benzyloxyindole with hydrogen in a solvent comprising ethanol, and in the presence of a catalyst at elevated temperature to provide a first reaction mixture comprising bazedoxifene free base, wherein the first reaction mixture is substantially free from hexamethylenimino benzyloxyindole; (b) treating said first reaction mixture with an antioxidant to provide a second reaction mixture; (c) filtering said second reaction mixture to provide a solution comprising bazedoxifene free base (i.e., bazedoxifene that is free of acetic acid); and (d) treating said solution with acetic acid to crystallize polymorphic Form D of bazedoxifene acetate.

In certain embodiments, in step (a) of the method described hereinabove, the solvent, in addition to ethanol, further comprises at least one solvent selected from the group consisting of ethyl acetate, acetone, cyclohexane and methanol, for example, ethanol-ethyl acetate, ethanol-acetone-cyclohexane, and ethanol-methanol-cyclohexane. In one embodiment, the solvent comprises ethanol and ethyl acetate.

In certain embodiments, step (a) of the method described hereinabove is completed in less than about 10 hours. In certain other embodiments, step (a) is completed in less than about 6 hours. In further embodiments, step (a) is completed in less than about 4 hours, for example, in less than about 3 hours or about 2 hours.

In certain embodiments, in step (a) of the method described hereinabove, the partial pressure of the hydrogen is at least about 4 bar. In certain other embodiments, in step (a), the partial pressure of the hydrogen is at least about 5 bar.

In certain embodiments, in step (a) of the method described hereinabove, the catalyst is a Pd/C catalyst. In one embodiment, the Pd/C catalyst used is in an amount less than about 12 mmol per mol of hexamethylenimino benzyloxyindole used. In another embodiment, the Pd/C catalyst used is in an amount less than about 6 mmol per mol of hexamethylenimino benzyloxyindole used. In another embodiment, the Pd/C catalyst used is in an amount less than about 3 mmol per mol of hexamethylenimino benzyloxyindole used.

In a further embodiment, the Pd/C catalyst has a total surface area (B.E.T) of more than about 1100 m$^2$/g. In one embodiment, the Pd/C catalyst has a total surface area (B.E.T) of more than about 1500 m$^2$/g. "B.E.T." refers to Brunauer-Emmett-Teller and is a surface area measurement technique applied to large surface area 1-20 m$^2$/g materials and based on adsorbed gas (e.g. N$_2$ at low temperature) as a function of pressure (monolayer coverage). See, e.g., G. A. Somorjai, *Principles of Surface Chemistry*, Prentice-Hall, Englewood Cliffs, N.J., 1972, p. 216.

In one embodiment, the Pd/C catalyst is non-reduced Pd on moist carbon, for example, BASF Catalyst 5% Pd on Carbon Powder DeLink code 57494652. In another embodiment, the Pd/C catalyst is BASF Catalyst 5% Pd on Carbon Powder catalyst code 57489193. Both catalysts can be purchased from BASF Catalysts LLC, Iselin, N.J.

These two exemplary catalysts present different physical-chemical characteristics. Table 2 below shows the principal characteristics of the two catalysts.

TABLE 2

| CATALYST: | 5% Pd on Carbon Power | 5% Pd on Carbon Power DeLink |
|---|---|---|
| CODE | 57489193 | 57494652 |
| Total Surface Area (B.E.T.) m$^2$/g | 1100 | 1500 |
| Particle Size Distribution (Laser) | 10% < 5 microns 50% < 18 microns 90% < 96 microns | 10% < 6 microns 50% < 38 microns 90% < 75 microns |
| Active Metal | Palladium | Palladium |
| Active Metal Content | 5% on dry basis [wt %] | 5% on dry basis [wt %] |
| Metal Distribution | Uniform | Eggshell |
| Type | Reduced/Moist | Unreduced/Moist |

In certain embodiments, step (a) of the method described hereinabove is carried out at a temperature of about 20° C. or higher. In certain other embodiments, step (a) is carried out at a temperature of about 30° C. or higher. In certain other embodiments, step (a) is carried out at a temperature of about 40° C. or higher. In certain embodiments, step (a) is carried out at a temperature of about 50° C.

In certain embodiments, in step (b) of the method described hereinabove, said antioxidant is ascorbic acid.

In certain embodiments, step (d) of the method described hereinabove is facilitated by seeding with polymorphic Form A of bazedoxifene acetate. In certain embodiments, step (d) is carried out at a temperature of about 40° C. In certain embodiments, step (d) is carried out at a temperature of about 30° C. or lower. In certain embodiments, step (d) is carried out at a temperature ranging from about 20° C. to about 35° C. In certain embodiments, step (d) is carried out at a temperature ranging from about 25° C. to about 30° C. In certain other embodiments, step (d) is carried out at a temperature ranging from about 28° C. to about 30° C.

In certain embodiments, step (d) of the method described hereinabove is completed in less than about 4 hours. In certain embodiments, step (d) is completed in less than about 3 hours. In certain embodiments, step (d) is completed in less than about 2 hours. In certain embodiments, step (d) is completed in about 0.1 hours to about 3 hours. In certain embodiments, step (d) is completed in about 0.5 hours to about 3 hours.

In certain embodiments, steps (a) through (d) of the method described hereinabove are conducted under inert atmosphere. Non-limiting examples of inert atmosphere include nitrogen, argon, and so forth.

In certain embodiments, in step (d) of the method described hereinabove, said resultant polymorphic Form D of bazedoxifene acetate is more than about 90% pure, more than about 95% pure, more than about 99% pure, or more than about 99.9% pure by weight.

Certain embodiments of the method described hereinabove further comprise isolating polymorphic Form D of bazedoxifene acetate by one or more of the steps of filtration, washing and drying.

In certain embodiments, the drying step in the isolation of polymorphic Form D, is conducted in an agitated filter dryer. An agitated filter dryer is useful in separating solids from liquid in a single vessel. Once the dryer is charged with slurry, pressure is either applied from the top of the filter dryer using a gas, such as nitrogen, or a vacuum is pulled from beneath the filter media, thereby forcing or pulling liquid through the cloth or mesh. Low pressures are generally used (e.g., about 1 bar) to keep the cake from becoming so compressed that the crystals fuse together. The liquid exits at the bottom of the vessel. While the crystals are collecting on the filter media, the smooth edge of the agitator acts to smooth the surface of the cake so there are no crevices. The other edge of the agitator, which can rotate in both directions, can have teeth for digging into the cake to help break it up and remove it from the filter media. The cake can be broken up and washed several times to remove trace solvents or impurities. Heat may be applied to the dryer to speed up the drying process. A suitable filter dryer can be purchased from a variety vendors, for example, OMCA Plants, Italy.

One skilled in the art will appreciate that the stirring frequency, instantaneous duration, total stirring duration and drying duration of the dryer may vary depending on the load of the product to be dried. In one embodiment, the stirring frequency is about 120 min., the instantaneous duration is about 2 min., the total stirring duration is about 18 min. and the drying duration is about 18 hours. In another embodiment, the stirring frequency is about 30 min., the instantaneous duration is about 1 min., the total stirring duration is about 38 min. and the drying duration is about 19 hours. In yet another embodiment, the stirring frequency is about 60 min., the instantaneous duration is about 1 min., the total stirring duration is about 18 min. and the drying duration is about 18 hours. In some embodiments, the wet product is left at low temperature (e.g., about 0° C.) under nitrogen flow without stirring for a short period of time (e.g., about 1 hour) to reduce the product humidity level before the beginning of the drying process.

In certain other embodiments, the drying step in the isolation of polymorphic Form D is conducted in a tumble dryer. The drying can be conducted in a tumble dryer under nitrogen, and/or vacuum conditions. A suitable tumble dryer can be purchased from a variety vendors, for example, Italvacuum CRIOX in Italy.

In certain embodiments, the drying step in the isolation of polymorphic Form D is conducted between about 20° C. to about 50° C. In certain embodiments, the drying step is conducted in at least about 20° C. In certain embodiments, the drying step is conducted in at least about 30° C. In certain embodiments, the drying step is conducted in at least about 40° C. In certain embodiments, the drying step is conducted in at least about 50° C.

In one aspect, the present disclosure is directed to polymorphic Form D of bazedoxifene acetate prepared according to the methods described herein. In certain embodiments, the polymorphic Form D of bazedoxifene acetate is more than about 90% pure, more than about 95% pure, more than about 99% pure, or more than about 99.9% pure. Throughout this disclosure, the purity of Form D of bazedoxifene acetate refers to polymorphic purity.

The present disclosure is further illustrated by the following examples. The examples are provided for illustrative purposes only. They are not to be construed as limiting the scope or content of the disclosure in any way.

EXAMPLES

Example 1

Preparation of Bazedoxifene Acetate Form D

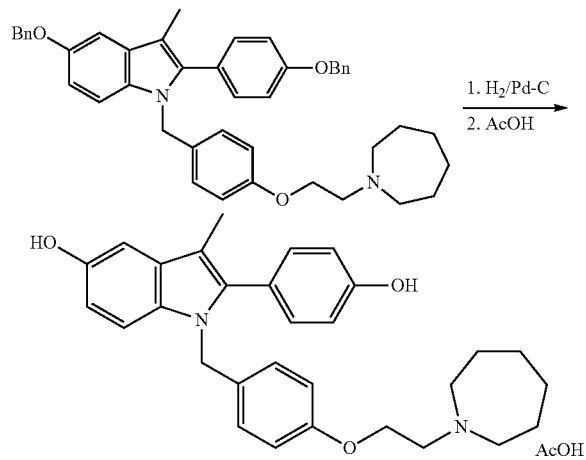

A slurry of hexamethyleniminobenzyloxy indole (35.7 g) (obtained as described in J. Med. Chem., 2001, 44, 1654-1657 and European Patent Application 00802183 filed Oct. 22, 1997) in 2.5 to 1 ethyl acetate and ethanol mixture (190 g) was hydrogenated in the presence of Pd/C (0.46 g), Delink, in a 5 bar hydrogen atmosphere, at 50° C. for 24 hrs. The reaction mixture was then added with ascorbic acid (0.27 g), filtrated through a Celite® pad, added with acetic acid (1.5 g) and kept at 30° C. under stirring. After 2 hrs self-nucleation occurred and additional acetic acid (3.3 g) was added. After 2 hrs at 30° C. under stirring, the precipitate was filtrated and dried in an oven under vacuum at 50° C. to obtain pure bazedoxifene acetate Form D (20 g).

Example 2

Preparation of Bazedoxifene Acetate Form D

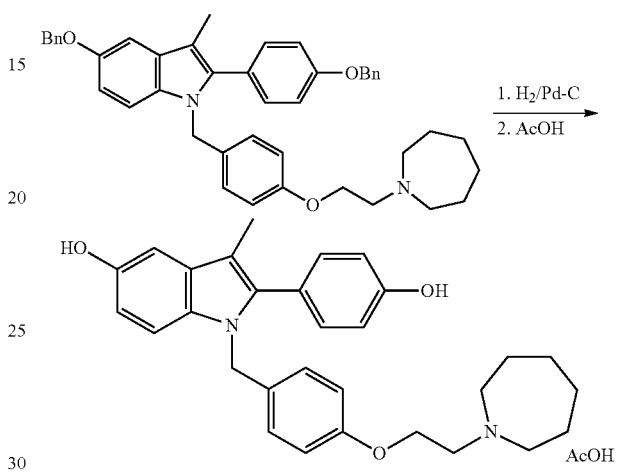

A slurry of hexamethyleniminobenzyloxy indole (5.6 g) in 2.5 to 1 ethyl acetate and ethanol mixture (30 g) was hydrogenated in the presence of Pd/C (0.1 g), Delink, in a 5 bar hydrogen atmosphere, at 50° C. for 24 hrs. The reaction mixture was then added with ascorbic acid (0.04 g), filtrated through a Celite® pad, added with acetic acid (0.17 g), seeded with bazedoxifene acetate Form A (7.6 mg, prepared as described in, for example, International Publication WO 05/100316, the disclosure of which is herein incorporated by reference in its entirety) and kept at 30° C. under stirring for 30 min. The formed precipitate was then filtrated out, and the mother liquor kept at 30° C. to follow Form D formation. After 18 hrs the obtained precipitate was filtrated and dried in an oven to yield pure bazedoxifene acetate Form D (1 g).

Example 3

Preparation of Bazedoxifene Acetate Form D from Form A

Bazedoxifene acetate Form A (1500 g) in a 3 to 1 ethyl acetate and water mixture (14.5 Kg) was combined with ascorbic acid (14.2 g) and sodium bicarbonate (250 g), and heated under stirring to approximately 60° C. in 1 hour. The temperature was maintained for approximately 1 hour. The solution was cooled to approximately 40° C. and allowed to stand for half an hour. The organic phase was separated and water (1000 g) was added. After stirring, the organic phase was separated and combined with ascorbic acid (14.2 g) and celite (43 g). The mixture was distilled under vacuum at approximately 50° C., cooled to 30° C., and a 13 to 1 ethanol and toluene mixture (7 Kg) was added. The reaction mixture was heated at 50° C. under stirring, and the temperature was maintained for approximately 30 minutes before cooling to 40° C. The suspension was filtered and the resulting filtrate was cooled to 30° C. before being charged stepwise with acetic acid (57.1 g), bazedoxifene acetate Form D (2.8 g), and acetic acid (197.1 g). The reaction mixture was cooled to 0° C. and the crystalline product was filtered and dried in an oven at approximately 50° C. under vacuum, affording about 1340 g of Bazedoxifene acetate Form D with about 99.9% purity.

Example 4

X-Ray Powder Diffraction (XRPD)

XRPD analyses were carried out by means of a Bruker diffractometer under the following working conditions:
Scan: from 3° to 40°; step size 0.01°
Source: Cu; 50 mA, 35 KV
Radiation: K($\alpha$1), K($\alpha$2)
Detector model: Lynx eye, Bruker
Collection time 1.5 sec per step
The XRPD results for Form D bazedoxifene acetate are shown in FIG. 1.

Example 5

Raman Spectroscopy

Raman spectra were acquired using an FT-Raman Thermofisher operated at a resolution of 4 cm$^{-1}$ and scanning from 250 to 4000 cm$^{-1}$. The Raman results for Form D bazedoxifene acetate are shown in FIG. 2.

Example 6

Differential Scanning Calorimetry (DSC)

DSC measurements were carried out on a Perkin Elmer Diamond equipped with a model ULSP90 intracooler; the samples (3-5 mg) were placed in aluminium closed pans. Heating was carried out at 5° C. min$^{-1}$ in the temperature range from 60° to 200° C. The DSC results for Form D bazedoxifene acetate are shown in FIG. 3.

Example 7

Solid State Characterization

1. Characterization of Solid Forms of Bazedoxifene Acetate

In order to assess the properties of the polymorphic forms, thermal analysis using differential scanning calorimetry (DSC), solubility measurement in aqueous and organic solvents and suspension inter-conversion studies were carried out.

Form D is differentiated from previously known crystalline Forms A and B by a unique powder x-ray diffraction pattern, Raman spectra and thermal properties. The thermal properties of the known solid forms of bazedoxifene acetate are listed in Table 3.

TABLE 3

Thermal Properties of Bazedoxifene Acetate Solid Forms

| Solid Form | Melting Point/Glass Transition (avg) [° C.] | Heat of Fusion (avg) [J/g] |
|---|---|---|
| Form A | 176-177 (176.5) | 95-100 (97.5) |
| Form B | 180-182 (181) | 115-120 (117.5) |
| Form D | 164-166 (165) | 120-125 (122.5) |
| Form C (amorphous) | 68-72 (glass transition) | N/A |

2. Solubility

Solubility of bazedoxifene acetate was measured by the dynamic dissolution method using Crystal-16 (Avantium Technologies BV, Netherlands), a medium-throughput tool for crystallization and solubility studies at a 1-mL scale which can accommodate 16 vials arranged in 4 rows. The profiles of the temperature and magnetic stirring speed for each row may be independently adjusted. The turbidity of each vial was monitored and plotted with the temperature profiles to determine dissolution and precipitation points of solids. A pre-weighed amount of solid and solvent were mixed together in clear glass vials, and were heated slowly (at 0.2° C./min). The dissolution temperature was recorded. The concentration of the solution (calculated based on the weight of solid and solvent) was treated as the saturation concentration at the recorded temperature, and solubility was calculated based on this concentration.

Figure 4:
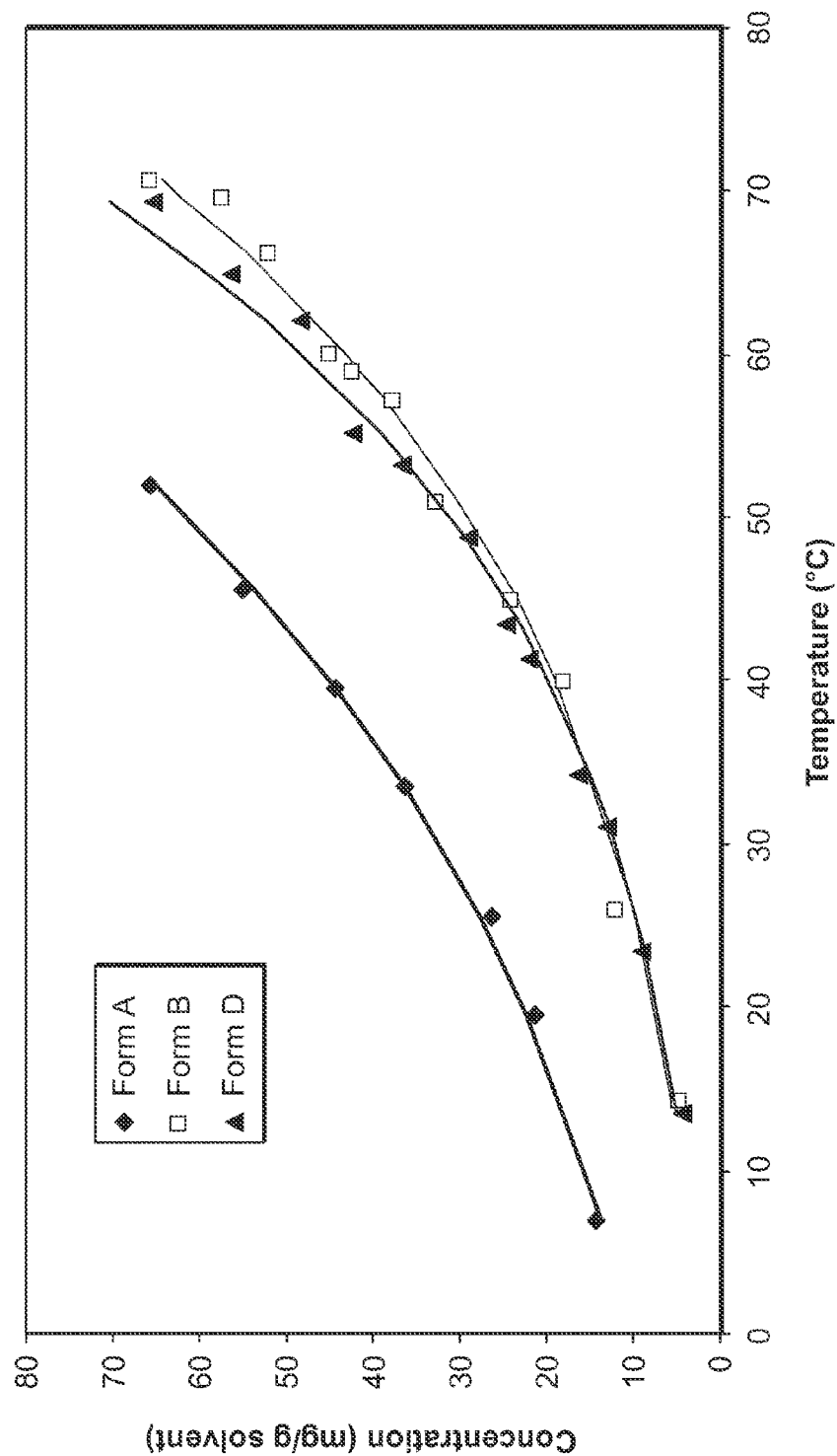
FIG. 4 shows the solubility of bazedoxifene acetate in the crystallization solvent mixture.
Figure 5:
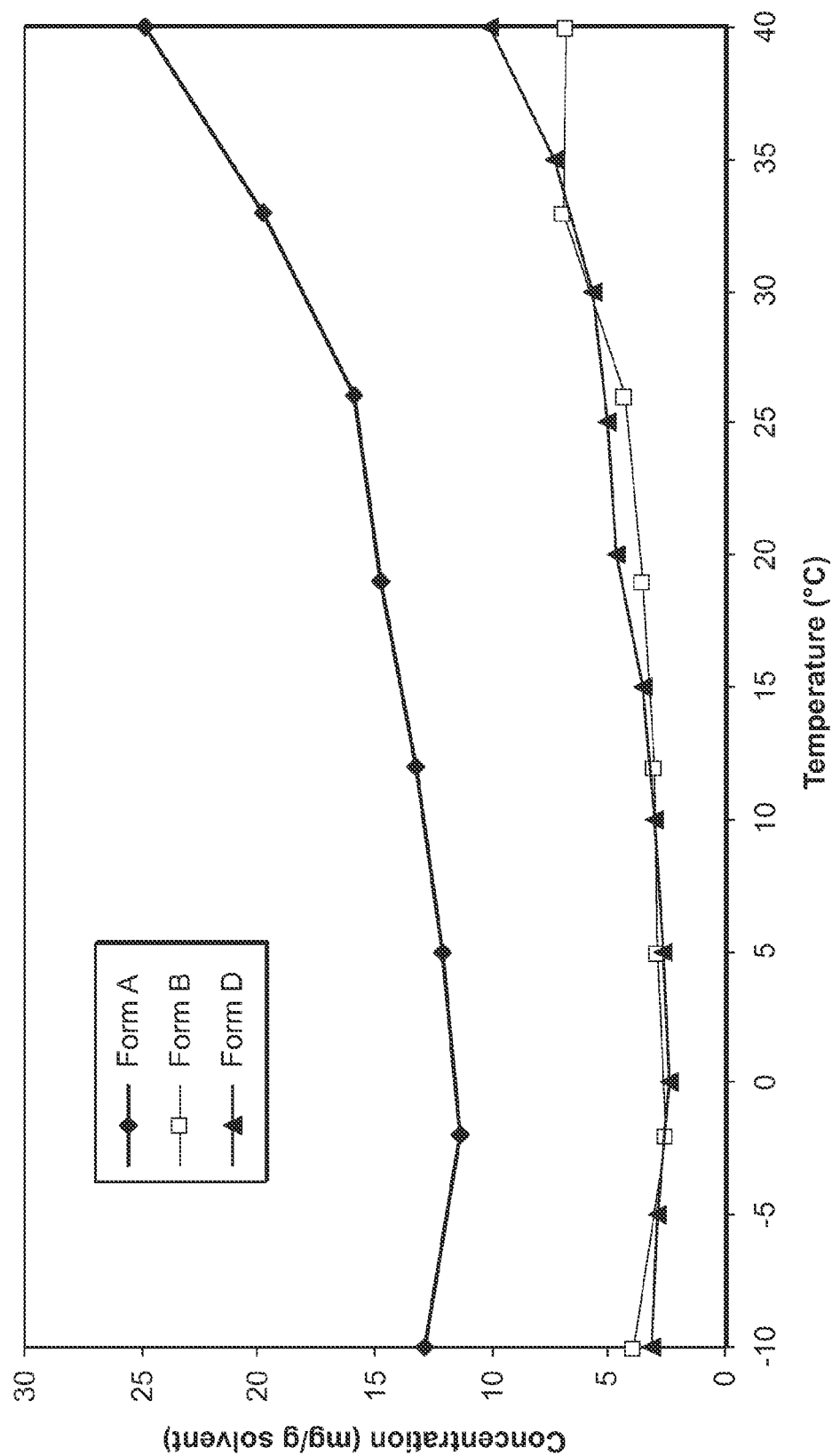
FIG. 5 shows the solubility of bazedoxifene acetate in the slurry test solvent.

Bazedoxifene acetate solubility was also measured using the HPLC method where an excess amount of solid bazedoxifene acetate was stirred in the solvent to obtain a suspension. The suspension was filtered after stirring for 30 minutes and the solution concentration was analyzed by HPLC. The measured solubility data for the two methods are plotted in FIGS. 4 and 5.

Two solvent mixtures were used in these studies:
1) Crystallization solvent (by weight): ethanol 66.53%, acetone 4.02%, cyclohexane 2.56%, ethyl acetate 22.26%, Toluene: 4.32%, water 0.3%, ascorbic acid 0.1%.
2) Slurry test solvent (by weight): ethanol 72.6% (denatured with acetone NMT 5.5% and cyclohexane NMT 3.5%), ethyl acetate 22.1%, acetic acid 0.7%, toluene: 4.2%, water 0.3%, and ascorbic acid 0.1%.

The solubility of Form A was found to be higher than Forms B and D at all conditions studied. Form D solubility in the crystallization solvent was very similar to Form B solubility, below about 30° C. Above this temperature, the solubility of Form D is slightly higher than that of Form B.

3. Stability of Polymorph Mixtures in Solvent Suspension

Suspension studies of the crystalline bazedoxifene acetate polymorphs were carried out to understand solvent-mediated form transformation. Experiments to determine the thermodynamically stable form at 0.5, 25 and 70° C. were performed using the three known crystalline Forms A, B and D (see Table 4). Mixtures of the three forms were suspended at a given temperature in a saturated solution of Form A and were equilibrated for several days. The solids were analyzed by XRPD after filtration.

TABLE 4

Summary of the Thermodynamic Stability Tests for Forms A, B and D

| Temperature [° C.] | Time [days] | Solvent | Form (XRPD) |
|---|---|---|---|
| 0.5 | 5 | methanol | Form D |
| 0.5 | 5 | water/acetonitrile 1:1 | Form D |
| 25 | 5 | methanol | Inconclusive, Form B and D |
| 25 | 5 | water/acetonitrile 1:1 | Form B, traces of Form D |
| 70 | 4 | benzyl alcohol, 500 ppm BHT | Form B |
| 70 | 4 | water/acetonitrile 1:1, 500 ppm BHT | Form B |

From this study, Form D is the most stable ansolvate known to date at 0.5° C. Form B is the most stable ansolvate known to date at 70° C. and likely the most stable ansolvate at 25° C.

Additional experiments to establish the kinetics of polymorph change were carried out using the industrial crystallization solvent system. A sample containing Form A and Form D was slurried at 25° C. in a solvent mixture reproducing the crystallization conditions of the process (ethanol denatured with cyclohexane/acetone, ethyl acetate, toluene and acetic acid). After two hours, the complete transition from Form A to Form D was observed (see Table 5). The data reported in the table below is a qualitative evaluation using DSC, taking a ratio of endotherm peaks.

TABLE 5

Kinetic Stability of Mixture Containing Form A and Form D

| Time [hours] | Form A [%]/Form D [%] |
|---|---|
| 0 | 30/70 |
| 2 | 0/100 (traces of Form B) |
| 4 | 0/100 (traces of Form B) |
| 20 | 0/100 (traces of Form B) |

A sample of Polymorph B was slurried at 25° C. in a solvent mixture reproducing the crystallization conditions of the process and seeded with polymorph D (5% w/w) (Table 6).

TABLE 6

Kinetic Stability of Form B Seeded with Form D

| Time [hours] | Form Change |
|---|---|
| 6 | No change |
| 24 | No change |
| 72 | No change |

A sample of Polymorph D was slurried at 25° C. in a solvent mixture reproducing the crystallization conditions of the process and seeded with polymorph B (5% w/w) (Table 7).

TABLE 7

Kinetic Stability of Form D Seeded with Form B

| Time [hours] | Note Form Change |
|---|---|
| 6 | No change |
| 24 | No change |
| 72 | No change |

From these interconversion experiments, the rate of conversion of Form A to Form D is shown to be rapid in the crystallization solvent. The rate of conversion of Form D to Form B and vice versa is very slow in the crystallization solvent mixture in agreement with the solubility data shown hereinabove.

4. Summary of Polymorph Screening and Stability Studies

Extensive polymorph screening has shown that bazedoxifene acetate can exist in multiple crystalline forms and in an amorphous state. Form B is the highest-melting bazedoxifene acetate polymorph. Solubility and form stability studies show that Form B is monotropically related to Form A. Form D, although lower melting than Form A is less soluble at 0-60° C. than Form A. Thus, Form A is meta-stable with respect to Form B and Form D under conditions encountered in the manufacturing process for bazedoxifene acetate.

Example 8

Detection of Bazedoxifene Acetate Form D

1. X-Ray Powder Diffraction

Figure 6:
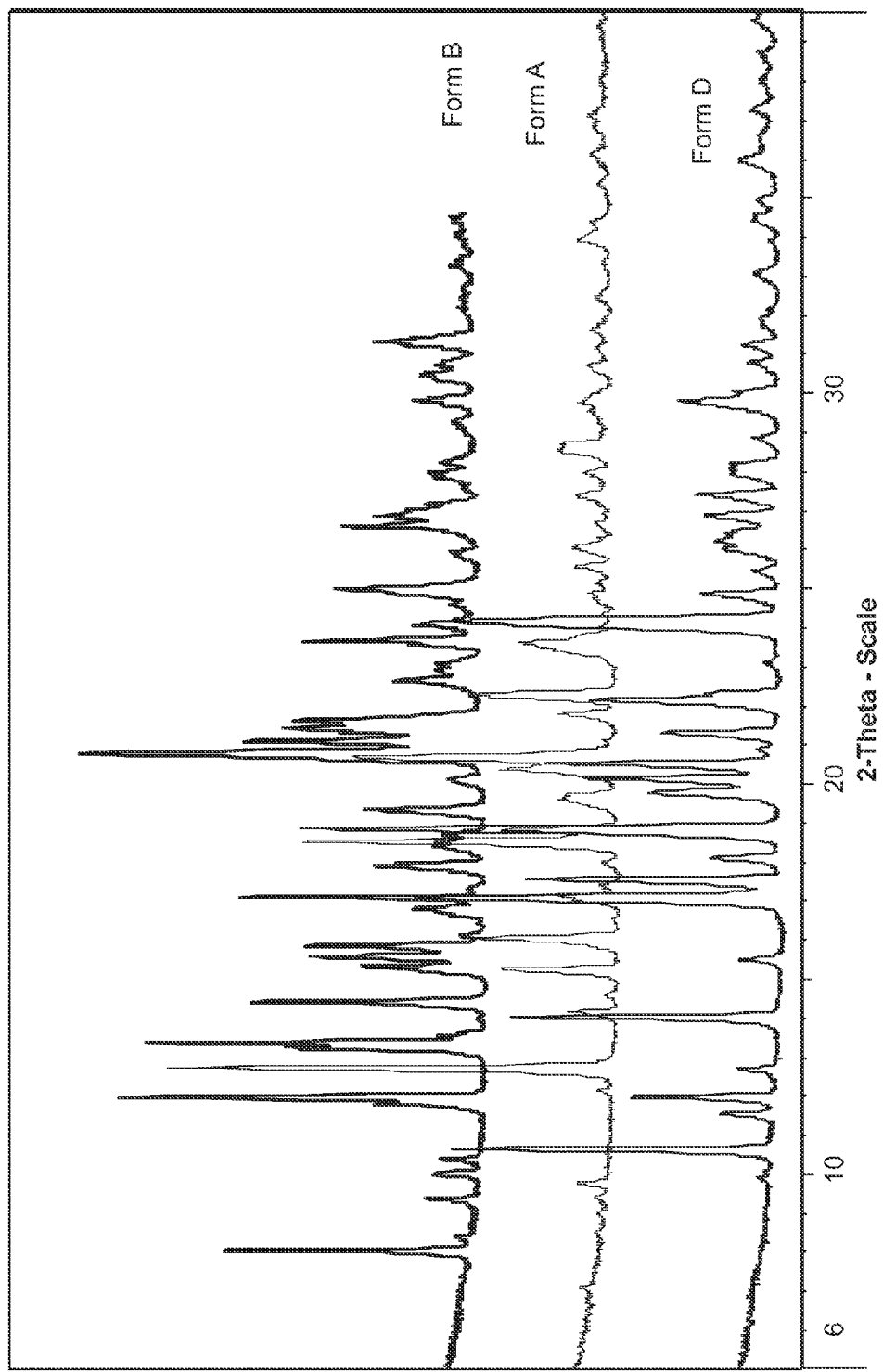
FIG. 6 shows XRPD diffractograms of bazedoxifene acetate Forms A, B, and D.

X-ray Powder Diffraction (XRPD) has been shown to discriminate between Forms A, B, and D. As shown in FIG. 6, the XRPD patterns have discriminating peaks for all three forms. Form D is identified by the characteristic peak at diffraction angle (2θ) of 10.6°.

The intensity (area) of the characteristic 10.6° Form D peak is directly proportional to the amount of Form D in the Form A active pharmaceutical ingredient ("API") sample. Quantitation of Form D was achieved by comparing the area of the Form D peak in the sample to that of samples with known Form D content (i.e., standards) to produce a calibration curve. The quantitation method has good linearity ($R^2$=0.9996) and good sensitivity; a detection limit of approximately 0.5% has been established. A Philips X'Pert MPD Powder X-ray Diffractometer equipped with an X'Celerator line detector was used.

XRPD provides specific, isolated peaks at 16.1° for Form A and at 10.6° for Form D. Relative peak area methodology was used to reduce variability of polymorph quantitation. Relative Form D peak area is the ratio of the Form D peak area at 10.6° to the sum of the Form D peak area at 10.6° and the Form A peak area at 16.1°. The peak areas were calculated through profile fitting using Topas software.

A linear calibration between Form D contents and relative Form D peak areas was established from spiked standards with known amount of Form D with a correlation coefficient of $R^2$=0.9986. Six spiked standards with Form D contents ranging from 0.5% to 5% were used. Multiple XRPD measurements and peak fittings were performed on each spiked standard to ensure reliability of the linear calibration.

This linear calibration was then used to calculate Form D content in a given bazedoxifene acetate sample which has Form D detected. Signal-to-noise ratio of no less than 3 (SNR≧3) was used to determine if Form D is present or detected.

A similar method using a Bruker X-ray diffractometer with a similar line detector could also be used to quantitate Form D content in bazedoxifene acetate API at a limit of detection of 0.5%.

2. Slurry Amplification Test

In order to detect polymorphic forms in bulk drug substance samples below the limit of detection of spectroscopic or x-ray techniques, a slurry amplification method was used. Polymorph stability studies have shown that Form D is thermodynamically more stable than Form A. A saturated suspension of Form A in the industrial crystallization solvent with seeds of Form D is shown to irreversibly convert to Form D due to the lower solubility of Form D. This is the basis for the slurry amplification test which was designed to detect 100-1000 ppm (0.01-0.1 wt %) of other polymorphic forms, such as Form D, in a sample of Form A by increasing the Form D amount to enable detection by XRPD.

Slurry amplification by suspension of the API at 25° C. was carried out by adding to a 100 mL glass reactor, equipped with a glass propeller stirrer, 30 g of crystallization solvent mixture (w/w %:72.6% EtOH, denatured with acetone and cyclohexane (ethanol assay NLT 91.0%, acetone content NMT 5.5%, cyclohexane content NMT 3.5%); 22.1% ethyl acetate; 0.7% acetic acid; 4.2% toluene; 0.3% water; 0.1% ascorbic acid) and 4.0 g of bazedoxifene acetate, under $N_2$ atmosphere. The concentration of bazedoxifene acetate (133 mg/g solvent) is significantly higher than the solubility of bazedoxifene acetate (see FIG. 3) in the solvent system at the test condition. The suspension was stirred (200 rpm) for 24 h at 25° C. After filtration and drying overnight at 45° C., the polymorphism of the solid sample was checked by XRPD.

Example 9

Effect of Isolation, Drying and Micronization on Form D Formation

To understand the origination of Form D in the process of bazedoxifene acetate Form A preparation, the process was sampled at various steps during crystallization, revealing that Form D was primarily formed in the crystallization operation, as seen in Table 8 (percentage values in Table 8 are estimated from DSC measurements and are only approximations). With Form D seeds present during crystallization, Form D amounts continued to grow through the isolation and drying operations.

TABLE 8

Characterization of Polymorph Using DSC During Crystallization and Isolation

| ID | Step | Form A % (DSC) | Form D % (DSC) |
|---|---|---|---|
| Sample-4 | After seeding, before addition of 2nd portion of acetic acid | 100% | 0% |
| Sample-5 | After seeding, and after addition of 40% of acetic acid | 84% | 16% |
| Sample-6 | After seeding and after addition of 80% of acetic acid | 34% | 66% |
| Sample-7 | End of addition of acetic acid | 78% | 22% |
| Sample-8 | Cooling step: sampling at 20° C. | 72% | 28% |
| Sample-9 | Cooling step: sampling at 10° C. | 63% | 37% |
| Sample-10 | Cooling step: sampling at 0° C. | 41% | 59% |
| Sample-11 | Cooling step: sampling after 1 hour at 0° C. | 37% | 63% |
| Sample-12 | Sampling after centrifugation | 2% | 98% |
| Sample-13 | Composite sample after discharge of tray dryers | Trace | 100% |

Additional monitoring showed that when no Form D was produced at the end of the crystallization, the dried bazedoxifene acetate remained free of Form D and the micronized bazedoxifene acetate also showed no detectable Form D content by XRPD (Table 9).

TABLE 9

Characterization of Polymorph During Crystallization and Isolation

| Sample ID | Step | Analysis (XRPD) |
|---|---|---|
| 1 | Crystallization, 30 min after seeding with Form A | Form A (no Form D detected) |
| 2 | Crystallization, after completed acetic acid addition | Form A (no Form D detected) |
| 3 | Wet product after centrifugation and washing | Form A (no Form D detected) |
| 4 | Dry product (unmilled) | Form A (no Form D detected) |
| 5 | Dry product (micronized) | Form A (no Form D detected) |

Laboratory scale experiments were conducted to further study the impact of filtration, drying and micronization on potential Form D growth.

Various modifications of the present disclosure, in addition to those embodiments specifically described herein, will be apparent to those skilled in the art from the foregoing description. Such modifications are also intended to fall within the scope of the appended claims. Each reference cited in the present application is incorporated herein by reference in its entirety.

We claim:

1. A crystalline polymorph (Form D) of bazedoxifene acetate having a powder X-ray diffraction pattern comprising characteristic peaks, in terms of 2Θ, at about 10.6°, 14.0°, 17.1°, 17.5° and 24.2°.

2. The polymorph of claim 1, wherein the polymorph has a temperature of glass transition between about 166° C. and about 168° C.

3. The polymorph of claim 1 with a Raman spectrum substantially as shown in FIG. 2.

4. The polymorph of claim 1 with a Raman spectrum comprising one or more characteristic peaks selected from about 1561 $cm^{-1}$, about 1589 $cm^{-1}$ and about 1613 $cm^{-1}$.

5. The polymorph of claim 1 with a differential scanning calorimetry trace substantially as shown in FIG. 3.

* * * * *